US00PP31641P3

(12) United States Plant Patent
Eggleton

(10) Patent No.: US PP31,641 P3
(45) Date of Patent: Apr. 7, 2020

(54) ***LAVANDULA* PLANT NAMED 'FW SPELLBOUND'**

(50) Latin Name: *Lavandula stoechas pedunculata*
Varietal Denomination: FW Spellbound

(71) Applicant: PLANT GROWERS AUSTRALIA, Wonga Park, Victoria (AU)

(72) Inventor: Steven Eggleton, Wandin North (AU)

(73) Assignee: Plant Growers Australia, Wonga Park (AU)

( * ) Notice: Subject to any disclaimer, the term of this patent is extended or adjusted under 35 U.S.C. 154(b) by 0 days.

(21) Appl. No.: 16/501,144

(22) Filed: Feb. 25, 2019

(65) Prior Publication Data

US 2019/0269057 P1 Aug. 29, 2019

(30) Foreign Application Priority Data

Feb. 26, 2018 (AU) ..... PBR 2018/040

(51) Int. Cl.
*A01H 5/02* (2018.01)
*A01H 6/50* (2018.01)

(52) U.S. Cl.
USPC ..... Plt./445
CPC ..... *A01H 6/502* (2018.05)

(58) Field of Classification Search
USPC ..... Plt./263.1, 445
See application file for complete search history.

(56) References Cited

PUBLICATIONS

PGA Plants website. https://www.pga.com.au/Plants/Collections/Lavender-Fairy-Wings.cshtml. 2 pages.*

* cited by examiner

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Lavandula* plant named 'FW Spellbound', characterized by its compact and broadly upright plant habit; freely branching growth habit, dense and bushy appearance; freely flowering habit; dark greyed purple-colored flowers with medium to large purple violet-colored sterile flower bracts arranged on short terminal spikes; and good garden performance.

2 Drawing Sheets

Botanical designation: *Lavandula stoechas pedunculata.*
Cultivar denomination: 'FW SPELLBOUND'.

CROSS-REFERENCED TO CLOSELY-RELATED APPLICATIONS

Applicant: Steven Eggleton
Title: *Lavandula* Plant Named 'FW Radiance'
Filed: Feb. 25, 2019
Ser. No. 16/501,145
Applicant: Steven Eggleton
Title: *Lavandula* Plant Named 'FW Whimsical'
Filed: Feb. 25, 2019
Ser. No. 16/501,146

This application claims priority to the Australia Plant Breeder's Rights application number 2018/040, filed Feb. 26, 2018.

BACKGROUND OF THE INVENTION

The present invention relates to a new and distinct *Lavandula* plant, botanically known as *Lavandula stoechas pedunculata*, commonly referred to as Spanish Lavender and hereinafter referred to by the name 'FW Spellbound'.

The new *Lavandula* plant is a product of a planned breeding program conducted by the Inventor in Wonga Park, Victoria, Australia. The objective of the breeding program was to develop new compact and freely-flowering *Lavandula* plants with good garden performance and attractive plant form and flower coloration.

The new *Lavandula* plant originated from a cross-pollination in October, 2009 of *Lavandula stoechas pedunculata* 'Papillon', not patented, as the female or seed, parent with *Lavandula stoechas pedunculata* 'Blueberry Ruffles', disclosed in U.S. Plant Pat. No. 18,305, as the male, or pollen, parent. The new *Lavandula* plant was discovered and selected by the Inventor as a single flowering plant within the progeny of the stated cross-pollination in a controlled greenhouse environment in Wonga Park, Victoria, Australia in October, 2014.

Asexual reproduction of the new *Lavandula* plant by softwood terminal cuttings in a controlled greenhouse environment in Wonga Park, Victoria, Australia since December, 2014 has shown that the unique features of this new *Lavandula* plant are stable and reproduced true to type in successive generations.

SUMMARY OF THE INVENTION

Plants of the new *Lavandula* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of the new *Lavandula* plant. These characteristics in combination distinguish 'FW Spellbound' as a new and distinct *Lavandula* plant:

1. Compact and broadly upright plant habit.
2. Freely branching growth habit, dense and bushy appearance.
3. Freely flowering habit.
4. Dark greyed purple-colored flowers with medium to large purple violet-colored sterile flower bracts arranged on short terminal spikes.
5. Good garden performance.

Plants of the new *Lavandula* differ primarily from plants of the female parent, 'Papillon', in the following characteristics:

1. Plants of the new *Lavandula* are more upright than and not as spreading as plants of 'Papillon'.
2. Plants of the new *Lavandula* have broader sterile flower bracts than plants of 'Papillon'.
3. Plants of the new *Lavandula* and 'Papillon' differ in sterile flower bract color as flowers of plants of the new *Lavandula* have purple violet-colored sterile flower bracts whereas flowers of plants of 'Papillon' have mauve-colored sterile flower bracts.

Plants of the new *Lavandula* differ primarily from plants of the male parent, 'Blueberry Ruffles', in the following characteristics:

1. Plants of the new *Lavandula* have shorter inflorescences than plants of 'Blueberry Ruffles'.
2. Plants of the new *Lavandula* have narrower sterile flower bracts than plants of 'Blueberry Ruffles'.
3. Plants of the new *Lavandula* and 'Blueberry Ruffles' differ in sterile flower bract color as flowers of plants of the new *Lavandula* have purple violet-colored sterile flower bracts whereas flowers of plants of 'Blueberry Ruffles' have more bluish-colored sterile flower bracts.
4. Plants of the new *Lavandula* have longer peduncles than plants of 'Blueberry Ruffles'.

Plants of the new *Lavandula* can be compared to plants of *Lavandula stoechas pedunculata* 'FW Radiance', disclosed in U.S. Plant patent application Ser. No. 16/501,145. Plants of the new *Lavandula* and 'FW Spellbound' differ primarily in flower color as flowers of plants of the new *Lavandula* are dark greyed purple in color with purple violet-colored sterile flower bracts whereas flowers of plants of 'FW Radiance' are light purple in color with red purple-colored sterile flower bracts.

Plants of the new *Lavandula* can be compared to plants of *Lavandula stoechas pedunculata* 'FW Whimsical', disclosed in U.S. Plant patent application Ser. No. 16/501,146. Plants of the new *Lavandula* and 'FW Whimsical' differ primarily in flower color as flowers of plants of the new *Lavandula* are dark greyed purple in color with purple violet-colored sterile flower bracts whereas flowers of plants of 'FW Whimsical' are light red purple in color with light red purple-colored sterile flower bracts.

Plants of the new *Lavandula* can be compared to plants of the *Lavandula stoechas* 'IBPRU41016', disclosed in U.S. Plant Pat. No. 30,083. In side-by-side comparisons, plants of the new *Lavandula* differ primarily from plants of 'IBPRU41016' in the following characteristics:

1. Plants of the new *Lavandula* more upright than plants of 'IBPRU41016'.
2. Plants of the new *Lavandula* have longer sterile flower bracts than plants of 'IBPRU41016'.
3. Plants of the new *Lavandula* have longer peduncles than plants of 'IBPRU41016'.

Plants of the new *Lavandula* can also be compared to plants of the *Lavandula stoechas* 'Sensation Purple', not patented. In side-by-side comparisons, plants of the new *Lavandula* differ primarily from plants of 'Sensation Purple' in the following characteristics:

1. Plants of the new *Lavandula* not as upright as plants of 'Sensation Purple'.
2. Plants of the new *Lavandula* have longer sterile flower bracts than plants of 'Sensation Purple'.
3. Plants of the new *Lavandula* and 'Sensation Purple' differ in sterile flower bract color as flowers of plants of the new *Lavandula* have purple violet-colored sterile flower bracts whereas flowers of plants of 'Sensation Purple' have purple-colored sterile flower bracts.

BRIEF DESCRIPTION OF THE PHOTOGRAPHS

The accompanying photographs illustrate the overall appearance of the new *Lavandula* plant showing the colors as true as it is reasonably possible to obtain in colored reproductions of this type. Colors in the photographs may differ slightly from the color values cited in the detailed botanical description which accurately describe the colors of the new *Lavandula* plant.

The photograph on the first sheet is a side perspective view of a typical flowering plant of 'FW Spellbound' grown in a container.

The photograph on the second sheet is a close-up view of typical inflorescences of 'FW Spellbound'.

DETAILED BOTANICAL DESCRIPTION

Plants used in the aforementioned photographs and following detailed description were grown in 1.5-liter containers during the late spring in an outdoor nursery in Wonga Park, Victoria, Australia and under cultural practices typical of commercial *Lavandula* production. Plants were pinched two times and were one year old when the photographs and description were taken. During the production of the plants, day temperatures ranged from 10° C. to 40° C. and night temperatures ranged from −1° C. to 20° C. In the following description, color references are made to The Royal Horticultural Society Colour Chart, 2007 Edition, except where general terms of ordinary dictionary significance are used.

Botanical classification: *Lavandula stoechas pedunculata* 'FW Spellbound'.

Parentage:

*Female, or seed, parent.*—*Lavandula stoechas pedunculata* 'Papillon', not patented.

*Male, or pollen, parent.*—*Lavandula stoechas pedunculata* 'Blueberry Ruffles', disclosed in U.S. Plant Pat. No. 18,305.

Propagation:

*Type.*—Terminal softwood vegetative cuttings.

*Time to initiate roots, summer.*—About ten days at temperatures about 24° C.

*Time to initiate roots, winter.*—About twelve days at temperatures about 21° C.

*Time to produce a rooted young plant, summer.*—About 24 to 28 days at temperatures ranging from 23° C. to 26° C.

*Time to produce a rooted young plant, winter*.—About 35 to 40 days at temperatures ranging from 15° C. to 18° C.

*Root description*.—Fine, fibrous; typically white to light brown in color, actual color of the roots is dependent on substrate composition, water quality, fertilizer type and formulation.

*Rooting habit*.—Freely branching; medium density.

Plant description:

*Plant and growth habit*.—Herbaceous perennial; compact and broadly upright plant habit; roughly globular to broadly ovate in overall shape; moderately vigorous growth habit; moderate growth rate; flowers arranged in verticillasters on terminal spikes.

*Plant height, soil level to top of foliar plane*.—About 16.3 cm.

*Plant height, soil level to top of floral plane*.—About 22.6 cm.

*Plant width*.—About 21.3 cm.

*Lateral branch description*.—Quantity per plant: About nine primary lateral branches each with about ten secondary branches developing per plant during the flowering season. Length: About 6.5 cm. Diameter: About 1.5 mm. Internode length: About 2.9 cm. Strength: Moderately strong. Aspect: Upright to somewhat outwardly. Texture and luster: Densely tomentose; slightly glossy. Color, developing: Close to 144B to 144C; at the internodes, between 143C and 144B. Color, developed: Close to 199B and 199C.

*Leaf description*.—Arrangement: Opposite, simple; sessile. Length: About 3.2 cm. Width: About 5 mm. Shape: Narrowly oblanceolate. Apex: Acute. Base: Cuneate. Margin: Entire; slightly to moderately revolute. Texture and luster, upper surface: Densely pubescent; matte. Texture and luster, lower surface: Moderately to densely pubescent; matte. Fragrance: Strongly aromatic, pungent. Venation pattern: Pinnate. Color: Developing leaves, upper surface: Close to 137B. Developing leaves, lower surface: Close to 138B. Fully expanded leaves, upper surface: Close to NN137B to NN137C; venation, close to 138A. Fully expanded leaves, lower surface: Close to 137B; venation, close to 138B.

Flower description:

*Flower type, arrangement and habit*.—Small single salverform flowers arranged in verticillasters on terminal cylindrical spikes; freely flowering habit with about 60 to 100 flowers developing in four to twelve whorls per inflorescence and about 50 inflorescences developing per plant; flowers with two-lobed upper lip and three-lobed lower lip; flowers face mostly outwardly on the spike.

*Natural flowering season*.—Relatively long flowering period; continuous from late winter to late spring/early summer in Australia.

*Flower longevity on the plant*.—Individual flowers last about one to two months on the plant; flowers not persistent.

*Fragrance*.—Resinous.

*Flower buds*.—Length: About 6 mm. Diameter: About 2 mm. Shape: Elliptic. Color: Close to 143A to 143B.

*Inflorescence height*.—About 2.3 cm, excluding terminal bracts.

*Inflorescence diameter*.—About 1.2 cm, excluding terminal bracts.

*Flower diameter*.—About 3.7 mm.

*Flower depth (height)*.—About 7 mm, including tube.

*Flower tube length*.—About 5 mm.

*Flower tube diameter*.—About 1 mm.

*Petals*.—Quantity and arrangement: Upper lip, two-lobed and lower lip, three-lobed. Length, upper and lower lips: About 1.8 mm. Width, upper and lower lips: About 1.7 mm. Shape, upper lip: Obovate. Shape, lower lip: Ovate. Apex, upper and lower lips: Obtuse, rounded. Margin, upper and lower lips: Entire; slightly undulate. Texture and luster, upper (inner) surface, upper and lower lips: Smooth, glabrous; slightly velvety; matte. Texture and luster, lower (outer) surface, upper and lower lips: Smooth, glabrous; slightly velvety; slightly glossy. Color, upper and lower lips: When opening, upper (inner) and lower (outer) surfaces: Close to N186B. Fully opened, upper (inner) and lower (outer) surfaces: Close to N186B; color does not change with development.

*Basal flower bracts*.—Quantity and arrangement: Each group of flowers is subtended by a single basal flower bract. Length: About 9 mm. Width: About 8 mm. Shape: Cordate. Apex: Cuspidate. Base: Cuneate. Margin; Entire. Texture, upper and lower surfaces: Smooth, glabrous. Color, upper and lower surfaces: Close to 143C.

*Sterile flower bracts*.—Quantity and arrangement: About four to eight sterile flower bracts at apex of spike. Length: About 2.8 cm. Width: About 1 cm. Shape: Oblong to oblanceolate. Apex: Broadly acute. Base: Obtuse. Margin: Entire; undulate. Texture and luster, upper and lower surfaces: Smooth, glabrous; matte. Color, upper and lower surfaces: Close to N81C becoming closer to N82A and N82C when developing and then becoming closer to N81C with subsequent development.

*Sepals*.—Quantity and arrangement: Five, fused into a campanulate tube. Calyx length: About 5 mm. Calyx diameter: About 2.3 mm. Shape: Lanceolate. Apex: Acute. Margin: Entire. Color, upper (inner) and lower (outer) surfaces: Close to 143A.

*Peduncles*.—Length: About 6.5 cm. Diameter: About 1.6 mm. Aspect: Mostly upright. Strength: Moderately strong. Texture and luster: Pubescent; matte. Color: Close to 144C.

*Reproductive organs*.—Stamens: Quantity per flower: Four. Anther shape: Reniform. Anther color: Greyish white. Pollen amount: If present, scarce. Pistils: Quantity per flower: One. Stigma shape: Club-shaped. Stigma color: Dark purple. Ovary color: Close to 143A to 143B.

*Seeds and fruits*.—To date, seed and fruit production has not been observed on plants of the new *Lavandula*.

Disease & pest resistance: Plants of the new *Lavandula* have been observed to be somewhat resistant to *Botrytis* (*Botrytis cinerea*) and to date have not been observed to be resistant to pests and other pathogens common to *Lavandula* plants.

Garden performance: Plants of the new *Lavandula* have exhibited good garden performance and to tolerate rain and wind and temperatures ranging from −2° C. to 42° C.

It is claimed:

1. A new and distinct *Lavandula* plant named 'FW Spellbound' as illustrated and described.

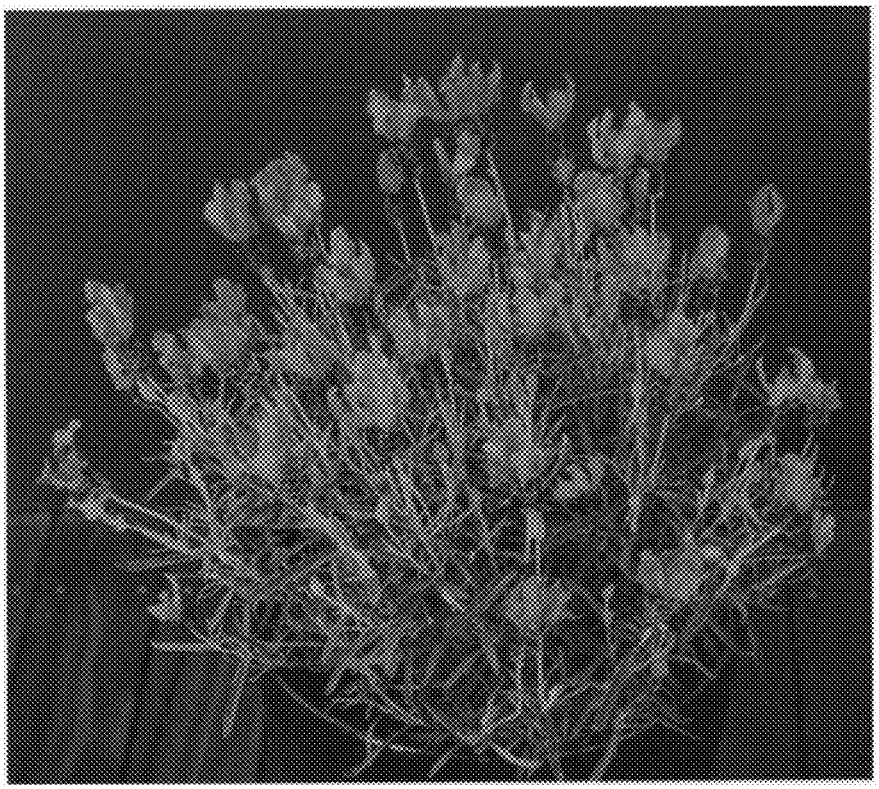

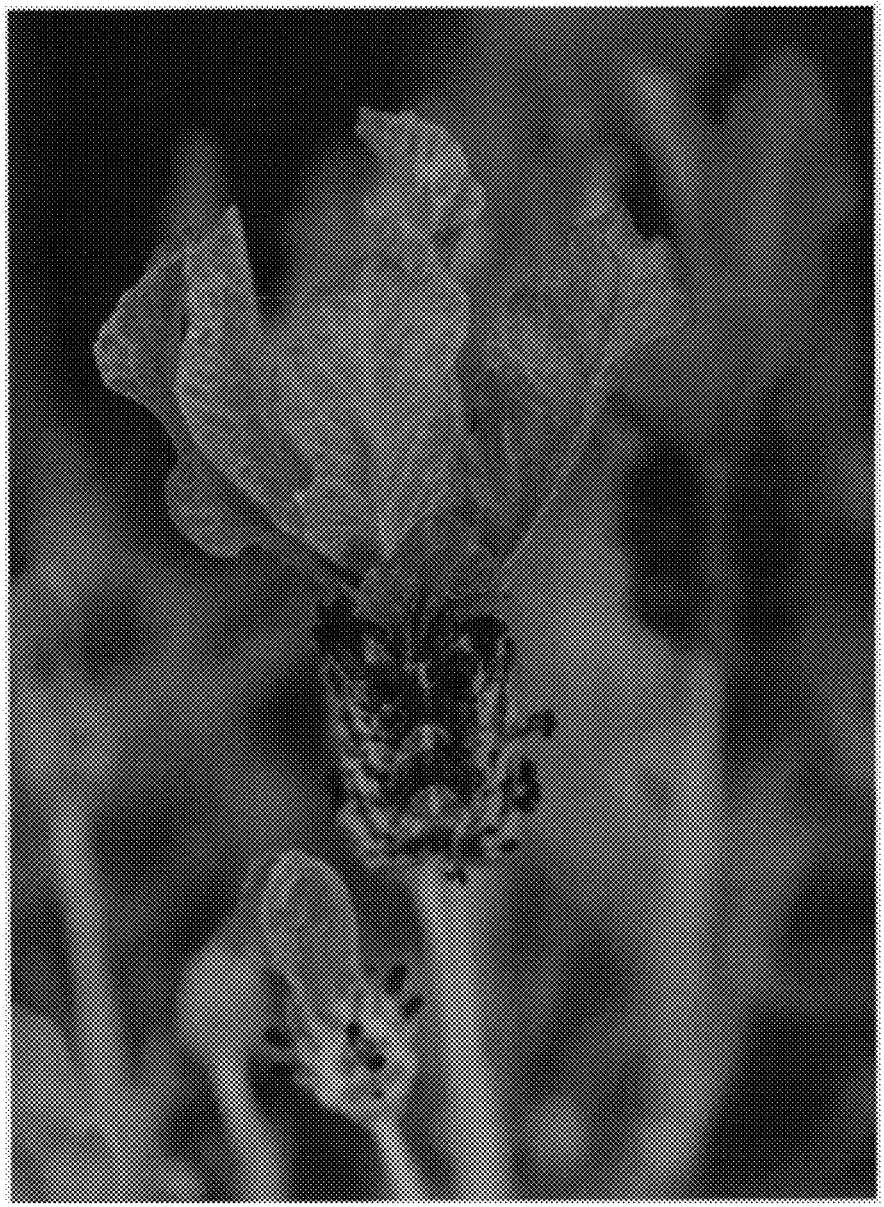

* * * * *